(12) United States Patent
Melzig et al.

(10) Patent No.: US 8,236,716 B2
(45) Date of Patent: Aug. 7, 2012

(54) PHOTOCHROMIC BENZOPYRANO-BENZOPYRANS WITH FURTHER FUSING

(75) Inventors: Manfred Melzig, Wessling (DE); Yven Rohlfing, Munich (DE); Udo Weigand, Munich (DE)

(73) Assignee: Rodenstock GmbH, Munich (DE)

( * ) Notice: Subject to any disclaimer, the term of this patent is extended or adjusted under 35 U.S.C. 154(b) by 234 days.

(21) Appl. No.: 12/672,589

(22) PCT Filed: Aug. 8, 2008

(86) PCT No.: PCT/EP2008/006575
§ 371 (c)(1),
(2), (4) Date: Feb. 8, 2010

(87) PCT Pub. No.: WO2009/024271
PCT Pub. Date: Feb. 26, 2009

(65) Prior Publication Data
US 2011/0201489 A1    Aug. 18, 2011

(30) Foreign Application Priority Data

Aug. 23, 2007 (DE) .................. 10 2007 039 994

(51) Int. Cl.
*C03C 4/00* (2006.01)
*G02B 5/23* (2006.01)

(52) U.S. Cl. ......... 501/13; 252/586; 264/1.32; 351/163; 524/96; 524/110; 544/150

(58) Field of Classification Search ................ 252/586; 427/164; 501/13; 524/96, 110; 544/124, 544/125, 148, 150; 546/167, 194, 196, 197, 546/280.7, 281.1, 284.1; 548/454, 518, 525, 548/526; 549/337, 362, 382, 58, 60; 264/1.32; 351/163

See application file for complete search history.

(56) References Cited

U.S. PATENT DOCUMENTS 6,022,495 A    2/2000  Kumar

FOREIGN PATENT DOCUMENTS

| CA | 2390770 | 3/2002 |
| WO | 0002884 | 1/2000 |
| WO | 0222594 | 3/2002 |

OTHER PUBLICATIONS

PCT/EP2008/006575; PCT International Preliminary Report on Patentability dated Feb. 24, 2010.
PCT/EP2008/006575; PCT International Search Report dated Nov. 17, 2008.

*Primary Examiner* — Bijan Ahvazi
(74) *Attorney, Agent, or Firm* — Renner, Otto, Boisselle & Sklar, LLP (57) ABSTRACT

The present invention relates to photochromic benzopyranobenzopyrans with additional fusion and to the use thereof in plastics of all types, in particular for ophthalmic purposes. The compounds according to the invention are photochromic benzopyran compounds which can also be regarded as derived from 9-oxa-9,10-dihydrophenanthrene.

24 Claims, 2 Drawing Sheets

PHOTOCHROMIC BENZOPYRANO-BENZOPYRANS WITH FURTHER FUSING

The present invention relates to photochromic benzopyranobenzopyrans with additional fusion and to the use thereof in plastics of all types, in particular for ophthalmic purposes. The compounds according to the invention are photochromic benzopyran compounds which can also be regarded as derived from 9-oxa-9,10-dihydrophenanthrene.

Various classes of dyestuffs which, on irradiating with light of certain wavelengths, in particular solar radiation, reversibly change their colour have been known for a long time. This results from the fact that these dye molecules are converted by light energy into an excited state, which they exit from again when the energy supply is interrupted and return to their initial state. These photochromic dyes include various pyran systems which have already been described in the state of the art with different parent systems and substituents.

Pyrans, especially naphthopyrans and larger ring systems derived therefrom, are at present the most widely employed class of photochromic compounds. Although already applied for as a patent for the first time in 1966 (U.S. Pat. No. 3,567,605), only in the 1990s could compounds be developed which appeared suitable for use in spectacle glass lenses. A suitable family of pyrans are, for example, the 2,2-diaryl-2H-naphtho[1,2-b]pyrans or the 3,3-diaryl-3H-naphtho[2,1-b]pyrans, which, in excited form, show different colourings, such as yellow, orange or orange-red.

Higher fused pyrans which, because of their larger ring system, absorb at longer wavelengths and produce red, purple and blue tints are of interest as an additional family of photochromic compounds. These can be systems derived either from the 2H-naphtho[1,2-b]pyrans or the 3H-naphtho[2,1-b] pyrans which result from the respective naphthopyran systems through fusion to the f side.

Diarylchromenes, in particular naphthopyrans or heterocyclically fused benzopyrans, which are substituted in the 6 position of the benzopyran with a phenyl ring or more generally an aromatic or heteroaromatic ring, which additionally is bridged via the 5 position of the benzopyran via at least one carbon atom, oxygen atom or nitrogen atom, are at present the most promising photochromic compounds.

If this bridging is produced only via one atom, this results in a five-membered ring fused to the benzopyran. Examples for a carbon atom are found in U.S. Pat. No. 5,645,767, U.S. Pat. No. 5,723,072 and U.S. Pat. No. 5,955,520 and examples for an oxygen atom are found in U.S. Pat. No. 6,018,059.

In U.S. Pat. No. 5,723,072, an unsubstituted, monosubstituted or disubstituted heterocyclic ring can additionally be fused on this parent system on the g, h, i, n, o or p side of the indenonaphthopyran. Indeno[1,2-f]naphtho[1,2-b]pyrans with a very large spread of possible substituents are therefore disclosed.

WO 96/14596, WO 99/15518, U.S. Pat. No. 5,645,767, WO 98/32037 and U.S. Pat. No. 5,698,141 disclose photochromic indeno-fused naphthopyran dyes derived from 2H-naphtho[1,2-b]pyran, the compositions comprising them and a process for their preparation. In U.S. Pat. No. 5,698,141, an unsubstituted, monosubstituted or disubstituted heterocyclic ring can additionally be fused on this parent system on the g, h, i, n, o or p side of the indenonaphthopyran. The substituent list, which is each time very extensive, also very specially includes spiro compounds, in fact such systems with a spiroheterocyclic group, in which, inclusive of the spiro atom, a 5- to 8-membered ring which always comprises two oxygen atoms is present on the 13-position of the parent system. An additional embodiment of the spiro ring occurs in Japanese application 344762/2000.

If this bonding is produced via two atoms, this results in a fused six-membered ring with varied possibilities for C, O and N alone. Compounds with $C=O$ and N—R (lactam bridge) are described in U.S. Pat. No. 6,379,591. Compounds with an unsubstituted $CH_2$—$CH_2$ bridge and a fused heterocycle in the 7,8-position of the underlying benzopyran are disclosed in U.S. Pat. No. 6,426,023.

U.S. Pat. No. 6,506,538 describes the carbocyclic analogous compounds, in which the hydrogen atoms in the bridge can be replaced by OH or $(C_1-C_6)$alkoxy or two hydrogen atoms on a carbon atom can be replaced by $=O$. Alternatively, one of the carbon atoms in the two-membered bridge can also be replaced by oxygen. These compounds are, in addition to others, described in WO 00/02884.

If this compound is produced through three atoms, this results in a fused 7-membered ring with a great many variational possibilities for insertion of heteroatoms. Compounds with a $CH_2$—$CH_2$—$CH_2$ bridge are described in U.S. Pat. No. 6,558,583. Here also, the hydrogen atoms in the bridge can be replaced by OH, $(C_1-C_6)$alkyl or $(C_1-C_6)$alkoxy or two hydrogen atoms on a carbon atom can be replaced by $=O$. With the same substitution pattern, they absorb at a shorter wavelength than the fused 6-membered rings.

US 2004/0094753 describes both compounds with a diatomic bridge and compounds with a triatomic bridge. The diatomic (carbon) bridge is in this connection in addition fused with a carbocycle or heterocycle. The triatomic bridge comprises three carbon atoms or two carbon atoms and an oxygen atom without additional fusion. Both rings can carry varied substituents.

However, the different photochromic dyes available in the state of the art have disadvantages which, when used in sun protection glass lenses, considerably restrict the comfort of the person wearing the glasses. First, the dyes exhibit an unsatisfactory long-wave absorption, both in the excited and nonexcited state. Secondly, an excessively high temperature sensitivity of the darkening is frequently present, it being possible for an excessively slow lightening to simultaneously occur. In addition, the dyes available in the state of the art often have an unsatisfactory service life and accordingly allow only a low durability of the sun protection glass lenses. The latter becomes noticeable in a rapidly declining performance and/or intense yellowing.

The object of the present invention is accordingly to make available a family of photochromic compounds which, limited to systems with a diatomic bridge, are to have markedly improved properties in comparison with the structures described in the state of the art. These can be found in the combination of long-wave absorption maximum of the closed form with steep edge to the visible wavelength region, high darkening performance, very rapid lightening reaction and very good resistance to light.

This object is achieved through the subject-matters characterized in the claims.

In particular, photochromic benzopyranobenzopyrans with additional fusion with the general formula (I) are made available:

(I)

in which at least one of the $R_6$, $R_7$ or $R_8$ radicals represents the following unit (A), (A)

with the proviso that $R_9$ or $R_{10}$ forms a bridging together with an $R_5$, $R_6$, $R_7$ or $R_8$ radical ortho to the coupling position, or $R_9$ and $R_{10}$, in the case of coupling of the above unit (A) via $R_6$, form two bridgings in each case together with the two $R_5$ and $R_7$ radicals ortho to the coupling position or, in the case of coupling of the above unit (A) via $R_7$, form two bridgings with the two $R_6$ and $R_8$ radicals ortho to the coupling position, the bridging via the $R_9$ or $R_{10}$ radicals being in each case one of those chosen from the group consisting of —$CR_{12}R_{13}$—, —O—, —S—, —N(Ph)-, —N($C_1$-$C_6$ alkyl)-, —O—$CR_{12}R_{13}$—, —S—$CR_{12}R_{13}$—, —$CR_{12}R_{13}$—$CR_{12}R_{13}$—, —$CR_{14}$=$CR_{15}$— or —$CR_{15}$=N—, or in which the $R_5$ radical with the $R_6$ radical or the $R_6$ radical with the $R_7$ radical or the $R_7$ radical with the $R_8$ radical or the $R_5$ radical with the $R_6$ radical and simultaneously the $R_7$ radical with the $R_8$ radical represent an unsubstituted, monosubstituted or disubstituted benzo, pyrido, furo or thieno ring, it being possible for the substituents to be chosen each time from the α group, consisting of a hydrogen atom, a ($C_1$-$C_6$) alkyl radical, a ($C_1$-$C_6$)alkylthio radical, a ($C_3$-$C_7$)cycloalkyl radical, which may exhibit one or more heteroatoms, such as, for example, O or S, a ($C_1$-$C_6$)alkoxy radical, a hydroxyl group, a trifluoro-methyl group, bromine, chlorine, fluorine or an unsubstituted, monosubstituted or disubstituted phenyl, phenoxy, benzyl, benzyloxy, naphthyl or naphthoxy radical, it being possible for the substituents again to be chosen from the α group;

and in which the $R_1$ and $R_2$ radicals represent, in each case independently of one another, a substituent chosen from the above α group; or the $R_1$ and $R_2$ radicals form an -A-($CH_2$)$_k$-D- group or -A-(C($CH_3$)$_2$)$_k$-D- group with k=1 or 2 bonded to the aromatic ring, A and D being chosen, independently of one another, from oxygen, sulphur, $CH_2$, C($CH_3$)$_2$ or C($C_6H_5$)$_2$ and it being possible for a benzo ring again to be fused to this -A-($CH_2$)$_k$-D- group; or the $R_1$ and $R_2$ radicals represent an unsubstituted, monosubstituted or disubstituted benzo or pyrido ring, it being possible for the substituents of which to be chosen from the α group;

the $R_3$ and $R_4$ radicals are either chosen, in each case independently of one another, from the α group or the $R_3$ and $R_4$ radicals, together with inclusion of the spiro carbon atom, form a 3- to 8-membered carbomonocyclic or heteromonocyclic Spiro ring optionally carrying one or more substituents from the α group, to which from one to three aromatic or heteroaromatic ring systems can be fused, the ring system being chosen, independently of one another, from the β group, consisting of benzene, naphthalene, phenanthrene, pyridine, quinoline, furan, thiophene, pyrrole, benzofuran, benzothiophene, indole and carbazole, which again can be substituted with one or more substituents from the α group, it being possible for two adjacent fused ring systems also to be linked to one another through an ortho,ortho' bridge, or the $R_3$ and $R_4$ radicals, together with inclusion of the spiro carbon atom, form a 7- to 12-membered carbobicyclic spiro ring or a 7- to 12-membered carbotricyclic spiro ring which can in each case optionally carry one or more substituents from the α group, the $R_5$, $R_6$, $R_7$, $R_8$, $R_9$ and $R_{10}$ radicals, provided that they do not form a bridging, and the $R_{11}$ radical represent, in each case independently of one another, a substituent chosen from the α group, or $R_5$ and $R_6$, in the case of coupling of the above unit (A) via $R_8$, represent a fused unsubstituted, monosubstituted or disubstituted benzo, naphtho or pyrido ring, the substituents of which can be chosen from the α group;

or two $R_{11}$ radicals in the ortho position with respect to one another form an -A-($CH_2$)$_k$-D- group or -A-(C($CH_3$)$_2$)$_k$-D- group with k=1 or 2, as defined above, bonded to the aromatic ring or two $R_{11}$ radicals in the ortho position with respect to one another represent an unsubstituted, monosubstituted or disubstituted benzo or pyrido ring, the substituents of which can be chosen from the α group;

the $R_{12}$, $R_{13}$, $R_{14}$ and $R_{15}$ radicals represent, in each case independently of one another, a substituent chosen from the α group, or $R_{12}$ and $R_{13}$ represent, together with an $R_{11}$ radical meta to the coupling position, a fused unsubstituted, monosubstituted or disubstituted benzo, naphtho or pyrido ring, the substituents of which can be chosen from the α group, this only being possible, with a bridging by means of the —O—$CR_{12}R_{13}$— or —S—$CR_{12}R_{13}$— groups, if $CR_{12}R_{13}$ is directly bonded to the phenyl ring carrying $R_{11}$, or in the case of coupling of the above unit (A) via $R_7$ and bridging via $R_6$, the $R_{12}$ and $R_{13}$ radicals, together with $R_5$, represent a fused unsubstituted, monosubstituted or disubstituted benzo, naphtho or pyrido ring, the substituents of which can be chosen from the α group, or, in the case of coupling of the above unit (A) via $R_8$ and bridging via $R_7$, the $R_{12}$ and $R_{13}$ radicals, together with $R_6$, represent a fused unsubstituted, monosubstituted or disubstituted benzo, naphtho or pyrido ring, the substituents of which can be chosen from the α group, or, in the case of coupling of the above unit (A) via $R_6$ and bridging via $R_7$, the $R_{12}$ and $R_{13}$ radicals, together with $R_8$, represent a fused unsubstituted, monosubstituted or disubstituted benzo, naphtho or pyrido ring, the substituents of which can be chosen from the α group, or $R_{14}$ and $R_{15}$ represent a fused unsubstituted, monosubstituted or disubstituted benzo, naphtho or pyrido ring, the substituents of which can be chosen from the α group;

m is 0, 1, 2 or 3, and

B and B' are chosen, independently of one another, from one of the following groups a), b) or c), a) being mono-, di- and trisubstituted aryl radicals, the aryl radical being phenyl, naphthyl or phenanthryl;

b) being unsubstituted, monosubstituted and disubstituted heteroaryl radicals, the heteroaryl radical being pyridyl, furanyl, benzofuranyl, thienyl, benzothienyl, 1,2,3,4-tetrahydro-carbazolyl or julolidinyl;

the substituents of the aryl or heteroaryl radicals in a) and b) being those chosen from the above-defined α group or the χ group, consisting of hydroxyl, 2-phenylethenyl unsubstituted, monosubstituted or disubstituted on the phenyl ring, (phenylimino)methylene unsubstituted, monosubstituted or disubstituted on the phenyl ring, (phenylmethylene)imino unsubstituted, monosubstituted or disubstituted on the phenyl ring, amino, mono ($C_1$-$C_6$)alkylamino, di($C_1$-$C_6$)alkylamino, mono- and diphenylamino unsubstituted, monosubstituted or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted, monosubstituted or disubstituted phenothiazinyl, unsubstituted, monosubstituted or disubstituted phenoxazinyl, unsubstituted, monosubstituted or disubstituted 1,2,3,4-tetra-hydroquinolinyl, unsubstituted, monosubstituted or disubstituted 2,3-dihydro-1,4-benzoxazinyl, unsubstituted, monosubstituted or disubstituted 1,2,3,4-tetrahydroisoquinolinyl, unsubstituted, monosubstituted or disubstituted phenazinyl, unsubstituted, monosubstituted or disubstituted carbazolyl, unsubstituted, monosubstituted or disubstituted 1,2,3,4-tetrahydrocarbazolyl and unsubstituted, monosubstituted or disubstituted 10,11-dihydrodibenz[b,f]azepinyl, it being possible for the substituent or substituents to be chosen, independently of one another, again from ($C_1$-$C_6$)alkyl, ($C_1$-$C_6$)alkoxy, bromine, chlorine or fluorine;

or two directly adjacent substituents representing a —Y—$(CX_2)_p$—Z— grouping, p being 1, 2 or 3, X being able to be hydrogen, $CH_3$ or $C_6H_5$ and Y and Z being able to be, independently of one another, oxygen, sulphur, N—($C_1$-$C_6$)alkyl, N—$C_6H_5$, $CH_2$, $C(CH_3)_2$ or $C(C_6H_5)_2$, it being possible for two or more adjacent carbon atoms of this —Y—$(CX_2)_p$—Z— grouping, in each case independently of one another, also to be part of a benzo ring system fused thereto which, in each case again, can exhibit one or more substituents chosen from the α group or the χ group;

or c) B and B' forming, together with the adjacent carbon atom of the pyran ring, an unsubstituted, monosubstituted or disubstituted 9,10-dihydroanthracene, fluorene, thioxanthene, xanthene, benzo[b]fluorene, 5H-dibenzo[a,d]cycloheptene or dibenzosuberone radical or a saturated hydrocarbon radical which is ($C_3$-$C_{12}$)spiromonocyclic, ($C_7$-$C_{12}$)spirobicyclic or ($C_7$-$C_{12}$)spirotricyclic, it being possible for the substituents of the unsaturated cyclene to be chosen, independently of one another, from the α group or the χ group.

The photochromic compounds derived from benzopyranobenzopyrans according to the invention exhibit, in comparison with systems at present available in the state of the art with a diatomic bridge, a clearly improved profile of properties, in particular an improved combination of very good service life and fast lightening rate. In addition, the compounds according to the invention show, in comparison with those with a monoatomic bridge, in addition to a faster lightening rate, also a lower solvatochromism. The compounds according to the invention show an equitable balance of longwave absorption maximum, high darkening performance, very fast lightening reaction and very good resistance to light.

Preferred photochromic benzopyranobenzopyrans with additional fusion according to the present invention exhibit the following general formula (II):

(II)

in which B, B', $R_3$, $R_4$, $R_5$, $R_6$, $R_7$ and $R_8$ are as defined above, $R_{16}$ is chosen from the α group and n is 0, 1, 2, 3 or 4.

The $R_3$ and $R_4$ radicals can, together with inclusion of the spiro carbon atom, form a 3- to 8-membered carbocyclic or heterocyclic ring to which from one to three aromatic or heteroaromatic ring systems can be fused, the ring system being chosen from the β group, consisting of benzene, naphthalene, phenanthrene, pyridine, quinoline, furan, thiophene, pyrrole, benzofuran, benzothiophene, indole and carbazole, which again can be substituted with one or more substituents from the α group. In this connection, two adjacent fused ring systems can also be linked to one another through an ortho, ortho' bridge, preferably an ethylene or a 1,2-ethenediyl bridge, so that, for example in the latter case, the following structural unit is present:

In a preferred embodiment, however, the $R_3$ and $R_4$ radicals are chosen, in each case independently of one another, from the α group.

If B or B' is a saturated hydrocarbon radical which is $C_3$-$C_{12}$ spiromonocyclic, $C_7$-$C_{12}$ spirobicyclic or $C_7$-$C_{12}$ spirotricyclic, $C_3$-$C_{12}$ spiromonocyclic is understood to mean a 3-membered to 12-membered ring familiar to a person skilled in the art. $C_7$-$C_{12}$ spirobicyclic systems are also well known to a person skilled in the art. Mention may in turn be made here, by way of example, of norbornane, norbornene, 2,5-norbornadiene, norcarane and pinane. An example of a $C_7$-$C_{12}$ spirotricyclic system is adamantane.

In an additional preferred embodiment, the B and B' radicals are chosen, independently of one another, from the group a) as defined above.

The substituents of the χ group which exhibit nitrogen atoms or carry amine groups are bonded via these to the phenyl, naphthyl or phenanthryl radical of the group a).

If, with regard to the substituents of the χ group which can be bonded to the phenyl, naphthyl or phenanthryl radical of the group a) for the B or B' radicals, two or more adjacent carbon atoms of this —Y—$(CX_2)_p$—Z— grouping can, in each case independently of one another, be part of a benzo ring system fused thereto, this means that the two methylene carbon atoms (—$CH_2$—$CH_2$—) then become part of a fused ring system. If, for example, two or three benzo rings are fused, it is possible, for example, for the following structural units, as mentioned below, to then be present here.

Naturally, it is also possible, however, for only one benzo ring fused via two adjacent carbon atoms of this —Y—$(CX_2)_p$—Z— grouping to be present.

Preferred photochromic benzopyranobenzopyran derivatives according to the present invention exhibit the following general formulae (III) or (IV):

(III)

(IV)

in which B, B', $R_3$, $R_4$, $R_5$, $R_8$, $R_{10}$ and $R_{16}$ are as defined above and W symbolizes the abovementioned bridging (the bridge is in these two cases formed from the $R_6$ and $R_9$ radicals and is as defined above, i.e. chosen from the group consisting of —$CR_{12}R_{13}$—, —O—, —S—, —N(Ph)-, —N($C_1$-$C_6$ alkyl)-, —O—$CR_{12}R_{13}$—, —S—$CR_{12}R_{13}$—, —$CR_{12}R_{13}$—$CR_{12}R_{13}$—, —$CR_{14}$=$CR_{15}$— or —$CR_{15}$=N—).

An additional particularly preferred embodiment according to the present invention is represented by compounds according to the following formulae (V), (VI) or (VII):

(V)

(VI)

(VII)

in which B, B', $R_3$, $R_4$, $R_5$, $R_6$, $R_7$, $R_8$, $R_{16}$ and n are as defined above, $R_{17}$ and $R_{18}$ are chosen from the α group and o and q are, independently of one another, 0, 1, 2, 3 or 4.

In comparison to the state of the art, i.e. WO 00/02884, the compounds according to the invention, with otherwise the same B, B', $R_3$ and $R_4$ substituents, exhibit a clearly longer-wavelength absorption band, both in the nonexcited and in the excited state. A longer-wavelength absorption in the nonexcited state has two important advantages on introducing the photochromic dyes, e.g. in plastic spectacle glass lenses. First, the compounds according to the invention react even if, with unfavourable atmospheric conditions, only very long-wavelength UV/sunlight (from 380 nm) is incident. It is obvious, from FIG. 1, that the compounds according to the invention in the nonexcited form absorb clearly more strongly at wavelengths of greater than 370 nm than in comparison with compounds of the state of the art. Because of that, the photochromic compounds according to the invention show a very good darkening performance, even with unfavourable conditions. Secondly, because of this, complete UV protection up to 400 nm is automatically achieved since the compounds according to the invention completely absorb the incident UV light.

It is unnecessary to add UV absorbers in the manufacture of sun protection glass lenses. This is a major advantage since admixed UV absorbers always absorb even a portion of the excitation light, so that glass lenses with UV absorbers always darken less strongly than without.

Figure 1:
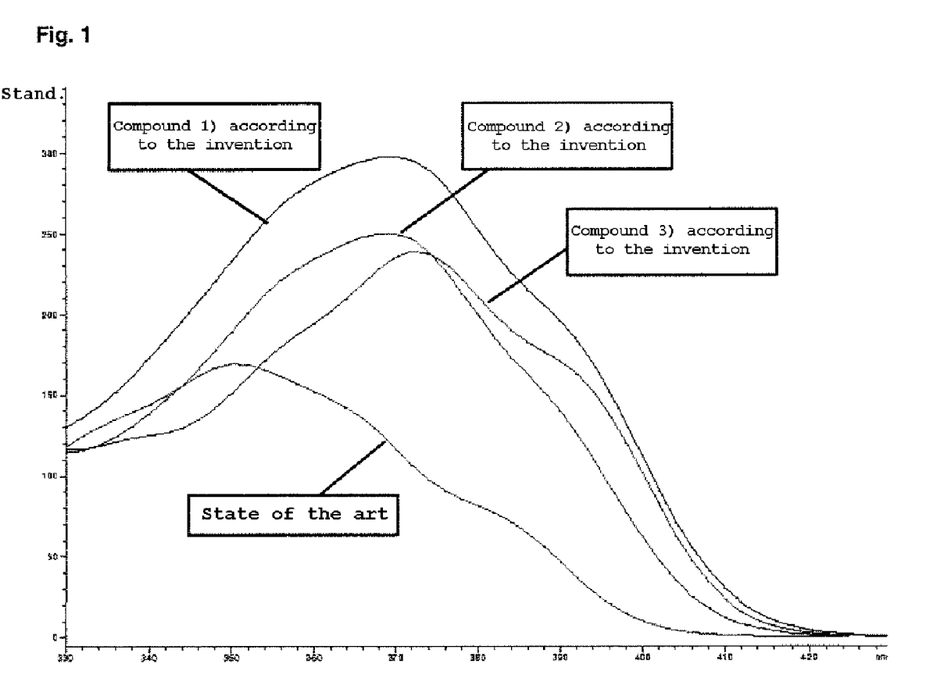
FIG. 1 is a graph comparing absorbance of compounds according to the invention at wavelengths of greater than 370 nm with compounds of the state of the art.

The structures of the compounds according to the invention represented in FIG. 1 and the extremely long-wavelength absorption maxima in the excited form thereof are obvious from the following Table 1 (in comparison with the state of the art from WO 00/02884):

TABLE 1

Longest wavelength absorption maxima in the excited state nonexcited (colourless)   excited (coloured)

A) State of the art (WO 00/02884)

| | $R_3$ | $R_4$ | $R_5$ | $R_6$ | $R_7$ | $R_8$ | B | B' | $\lambda_{max}$ (excited) |
|---|---|---|---|---|---|---|---|---|---|
| | H | H | H | H | H | H | phenyl | 4-(N-morpholinyl)-phenyl | 565 nm |

B) Compounds according to the invention

| Compound | $R_3$ | $R_4$ | $R_5$ | $R_6$ | $R_7$ | $R_8$ | B | B' | $\lambda_{max}$ (excited) |
|---|---|---|---|---|---|---|---|---|---|
| 1) | H | H | H | H | benzo | phenyl | 4-(N-morpholinyl)-phenyl | 590 nm |

TABLE 1-continued

| | | | | | | | | |
|---|---|---|---|---|---|---|---|---|
| 2) | H | H | benzo | H | H | phenyl | 4-(N-morpholinyl)-phenyl | 585 nm |
| 3) | H | H | H | benzofuro (according to formula (III)) | H | phenyl | 4-(N-morpholinyl)-phenyl | 585 nm |

In order to measure the properties of the photochromic dyes according to the invention and of the compound of the state of the art (see above), 500 ppm of the dye were each time dissolved in an acrylate monomer matrix and polymerization was carried out thermally using a temperature programme after addition of a polymerization initiator. The transmission properties of the plastic glass lenses thus prepared (thickness 2 mm) were subsequently measured according to DIN EN ISO 8980-3.

The compounds according to the invention can be used in plastic materials or plastic articles of any type and shape for a multitude of end uses for which photochromic behaviour is important. Use may be made, in this connection, of a dye according to the present invention or a mixture of such dyes. By way of example, the photochromic benzopyranobenzopyran dyes according to the invention can be used in lenses, in particular ophthalmic lenses, glass lenses for spectacles of all types, such as, for example, ski goggles, sunglasses, motorcycle goggles, visors of safety helmets, and the like. Furthermore, the photochromic benzopyranobenzopyrans according to the invention can be used, for example, also as sun protection in vehicles and living spaces in the form of windows, protective screens, covers, roofs or the like.

In order to prepare such photochromic articles, the photochromic benzopyranobenzopyrans according to the invention can be applied to a polymer material, such as an organic plastic material, or be embedded therein, through different processes described in the state of the art, such as already given in WO 99/15518.

A distinction is made in this context between "bulk colouring processes" and "surface colouring processes". A bulk colouring process comprises, for example, the dissolution or dispersion of the photochromic compound or compounds according to the present invention in a plastic material, e.g. through the addition of the photochromic compound(s) to a monomeric material, before the polymerization takes place. A further possibility for the preparation of a photochromic article is the penetration of the plastic material or materials with the photochromic compound(s) by immersing the plastic material in a hot solution of the photochromic dye or dyes according to the present invention or, for example, also a heat transfer process. The photochromic compound(s) can, for example, also be provided in the form of a separate layer between adjoining layers of the plastic material, e.g. as part of a polymer film. Furthermore, application of the photochromic compound(s) as part of a coating situated on the surface of the plastic material is also possible. The expression "penetration" is in this connection to mean the migration of the photochromic compound(s) into the plastic material, e.g. through the solvent-assisted transfer of the photochromic compound(s) into a polymer matrix, vapour phase transfer or other such surface diffusion processes. Advantageously, such photochromic articles, such as, e.g., spectacle glass lenses, can be prepared not only using normal bulk colouring but also, in the same way, using surface colouring, it being possible to achieve, in the latter variant, a surprisingly lower tendency to migrate. This is especially advantageous in subsequent refining steps since—e.g., with an antireflection coating through the lower back diffusion in vacuo—coating separations and similar defects are drastically reduced.

On the whole, it is possible, on the basis of the photochromic benzopyranobenzopyrans according to the invention, to apply any compatible (acceptable chemically and in terms of colour) colouring, i.e. dye, to the plastic material or to embed it therein, in order to satisfy both aesthetic standpoints and also medicinal or stylish aspects. The dye(s) specifically chosen can therefore vary depending on the intended actions and requirements.

Figure 2:
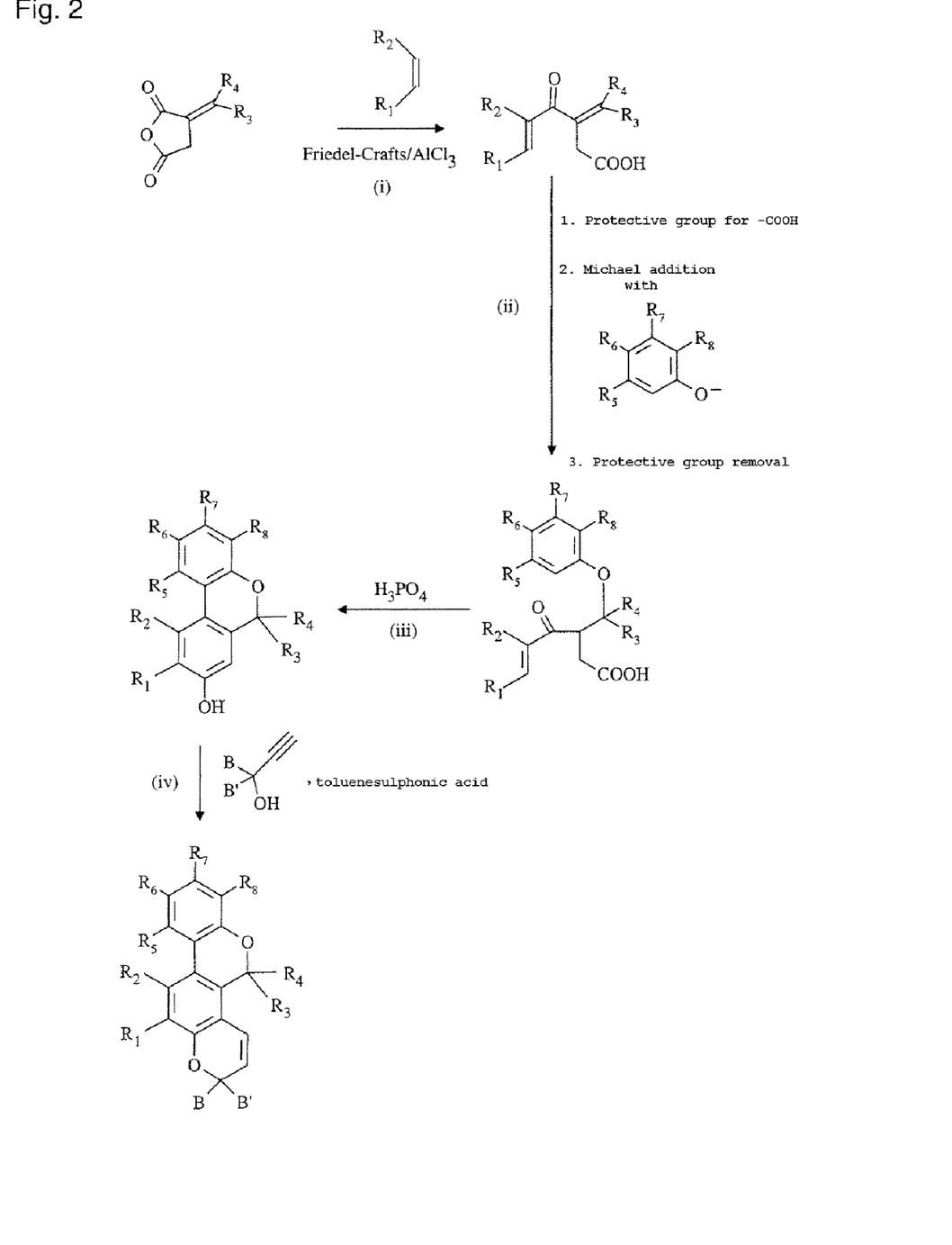
FIG. 2 depicts an exemplary synthetic scheme for preparation of photochromic compounds according to an embodiment of the invention.

The photochromic compounds according to the invention can be prepared according to the following exemplary synthetic scheme, as shown in FIG. 2.

Suitably substituted methylidenesuccinic anhydrides are subjected, in a first step, to a Friedel-Crafts reaction with suitably substituted 1,2-ethylenes (step (i)). The —COOH group of the intermediate resulting therefrom is subsequently protected and this intermediate is subjected to a Michael addition with appropriately substituted phenoxide derivatives (step (ii)). After removal of the carboxylic acid protective group, appropriately substituted 9-oxa-9,10-dihydrophenanthrene derivatives are formed via intramolecular cyclization by means of phosphoric acid (step (iii)). Subsequently, these substituted 9-oxa-9,10-dihydrophenanthrene derivatives are reacted with suitably substituted 2-propyn-1-ol derivatives according to step (iv) to give the compounds according to the invention.

The invention claimed is:

1. Photochromic benzopyranobenzopyrans with additional fusion with the general formula (I):

(I)

in which
at least one of the $R_6$, $R_7$ or $R_8$ radicals represents the following unit (A), (A)

with the proviso that $R_9$ or $R_{10}$ forms a bridging together with an $R_5$, $R_6$, $R_7$ or $R_8$ radical ortho to the coupling position, or $R_9$ and $R_{10}$, in the case of coupling of the above unit (A) via $R_6$, form two bridgings in each case together with the two $R_5$ and $R_7$ radicals ortho to the coupling position or, in the case of coupling of the above unit (A) via $R_7$, form two bridgings with the two $R_6$ and $R_8$ radicals ortho to the coupling position, the bridging via the $R_9$ or $R_{10}$ radicals being in each case one of those chosen from the group consisting of —$CR_{12}R_{13}$—, —O—, —S—, —N(Ph)-, —N($C_1$-$C_6$ alkyl)-, —O—$CR_{12}R_{13}$—, —S—$CR_{12}R_{13}$—, —$CR_{12}R_{13}$—$CR_{12}R_{13}$—, —$CR_{14}$=$CR_{15}$— or —$CR_{15}$=N—, or in which the $R_5$ radical with the $R_6$ radical or the $R_6$ radical with the $R_7$ radical or the $R_7$ radical with the $R_8$ radical or the $R_5$ radical with the $R_6$ radical and simultaneously the $R_7$ radical with the $R_8$ radical represent an unsubstituted, monosubstituted or disubstituted benzo, pyrido, furo or thieno ring, wherein, when substituted, the substituents may be chosen each time from the α group, wherein the α group consists of a hydrogen atom, a ($C_1$-$C_6$)alkyl radical, a ($C_1$-$C_6$)alkylthio radical, a ($C_3$-$C_7$)cycloalkyl radical, wherein each radical may contain one or more O or S heteroatoms, a ($C_1$-$C_6$)alkoxy radical, a hydroxyl group, a trifluoromethyl group, bromine, chlorine, fluorine or an unsubstituted, monosubstituted or disubstituted phenyl, phenoxy, benzyl, benzyloxy, and naphthyl or naphthoxy radical, wherein, when substituted, the substituents again may be chosen from the α group;

and in which the $R_1$ and $R_2$ radicals represent, in each case independently of one another, a substituent chosen from the above α group; or the $R_1$ and $R_2$ radicals form an -A-$(CH_2)_k$-D- group or -A-$(C(CH_3)_2)_k$-D- group with k=1 or 2 bonded to the aromatic ring, A and D being chosen, independently of one another, from oxygen, sulphur, $CH_2$, $C(CH_3)_2$ or $C(C_6H_5)_2$ and wherein a benzo ring may be fused to this -A-$(CH_2)_k$-D- group; or the $R_1$ and $R_2$ radicals represent an unsubstituted, monosubstituted or disubstituted benzo or pyrido ring wherein, when substituted, the substituents may be chosen from the α group;

the $R_3$ and $R_4$ radicals are either chosen, in each case independently of one another, from the α group or the $R_3$ and $R_4$ radicals, together with inclusion of the spiro carbon atom, form a 3- to 8-membered carbomonocyclic or heteromonocyclic spiro ring optionally carrying one or more substituents from the α group, to which from one to three aromatic or heteroaromatic ring systems can be fused, the ring system being chosen, independently of one another, from the β group, wherein the β group consists of benzene, naphthalene, phenanthrene, pyridine, quinoline, furan, thiophene, pyrrole, benzofuran, benzothiophene, indole and carbazole, which again can be substituted with one or more substituents from the α group, wherein two adjacent fused ring systems also may be linked to one another through an ortho,ortho' bridge, or the $R_3$ and $R_4$ radicals, together with inclusion of the spiro carbon atom, form a 7- to 12-membered carbobicyclic spiro ring or a 7- to 12-membered carbotricyclic spiro ring which can in each case optionally carry one or more substituents from the α group, the $R_5$, $R_6$, $R_7$, $R_8$, $R_9$ and $R_{10}$ radicals, provided that they do not form a bridging, and the $R_{11}$ radical represent, in each case independently of one another, a substituent chosen from the α group, or $R_5$ and $R_6$, in the case of coupling of the above unit (A) via $R_8$, represent a fused unsubstituted, monosubstituted or disubstituted benzo, naphtho or pyrido ring, the substituents of which can be chosen from the α group;

or two $R_{11}$ radicals in the ortho position with respect to one another form an -A-$(CH_2)_k$-D- group or -A-$(C(CH_3)_2)_k$-D- group with k=1 or 2, as defined above, bonded to the aromatic ring or two $R_{11}$ radicals in the ortho position with respect to one another represent an unsubstituted, monosubstituted or disubstituted benzo or pyrido ring, wherein, when substituted, the substituents may be chosen from the α group;

the $R_{12}$, $R_{13}$, $R_{14}$ and $R_{15}$ radicals represent, in each case independently of one another, a substituent chosen from the α group, or $R_{12}$ and $R_{13}$ represent, together with an $R_{11}$ radical meta to the coupling position, a fused unsubstituted, monosubstituted or disubstituted benzo, naphtho or pyrido ring, the substituents of which can be chosen from the α group, wherein, when substituted, with a bridging by means of the —O—$CR_{12}R_{13}$— or —S—$CR_{12}R_{13}$— groups, if $CR_{12}R_{13}$ is directly bonded to the phenyl ring carrying $R_{11}$, or in the case of coupling of the above unit (A) via $R_7$ and bridging via $R_6$, the $R_{12}$ and $R_{13}$ radicals, together with $R_5$, represent a fused unsubstituted, monosubstituted or disubstituted benzo, naphtho or pyrido ring, the substituents of which can be chosen from the α group, or, in the case of coupling of the above unit (A) via $R_8$ and bridging via $R_7$, the $R_{12}$ and $R_{13}$ radicals, together with $R_6$, represent a fused unsubstituted, monosubstituted or disubstituted benzo, naphtho or pyrido ring, the substituents of which can be chosen from the α group, or, in the case of coupling of the above unit (A) via $R_6$ and bridging via $R_7$, the $R_{12}$ and $R_{13}$ radicals, together with $R_8$, represent a fused unsubstituted, monosubstituted or disubstituted benzo, naphtho or pyrido ring, the substituents of which can be chosen from the α group, or $R_{14}$ and $R_{15}$ represent a fused unsubstituted, monosubstituted or disubstituted benzo, naphtho or pyrido ring, the substituents of which can be chosen from the α group;

m is 0, 1, 2 or 3, and

B and B' are chosen, independently of one another, from one of the following groups a), b) or c), a) being mono-, di- and trisubstituted aryl radicals, the aryl radical being phenyl, naphthyl or phenanthryl;

b) being unsubstituted, monosubstituted and disubstituted heteroaryl radicals, the heteroaryl radical being pyridyl, furanyl, benzofuranyl, thienyl, benzothienyl, 1,2,3,4-tetrahydrocarbazolyl or julolidinyl;

the substituents of the aryl or heteroaryl radicals in a) and b) being chosen from the α group or the χ group, wherein the χ group consists of hydroxyl, 2-phenylethenyl unsubstituted, monosubstituted or disubstituted on the phenyl ring, (phenylimino)methylene unsubstituted, monosubstituted or disubstituted on the phenyl ring, (phenylmethylene)imino unsubstituted, monosubstituted or disubstituted on the phenyl ring, amino, mono($C_1$-$C_6$)alkylamino, di($C_1$-$C_6$)alkylamino, mono- and diphenylamino unsubstituted, monosubstituted or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted, monosubstituted or disubstituted phenothiazinyl, unsubstituted, monosubstituted or disubstituted phenoxazinyl, unsubstituted, monosubstituted or disubstituted 1,2,3,4-tetrahydroquinolinyl, unsubstituted, monosubstituted or disubstituted 2,3-dihydro-1,4-benzoxazinyl, unsubstituted, monosubstituted or disubstituted 1,2,3,4-tetrahydroisoquinolinyl, unsubstituted, monosubstituted or disubstituted phenazinyl, unsubstituted, monosubstituted or disubstituted carbazolyl, unsubstituted, monosubstituted or disubstituted 1,2,3,4-tetrahydrocarbazolyl and unsubstituted, monosubstituted or disubstituted 10,11-dihydrodibenz[b,f]azepinyl, wherein the substituent or substituents may be chosen, independently of one another, from ($C_1$-$C_6$)alkyl, ($C_1$-$C_6$)alkoxy, bromine, chlorine or fluorine;

or two directly adjacent substituents representing a —Y—$(CX_2)_p$—Z— grouping, p being 1, 2 or 3, X may be hydrogen, $CH_3$ or $C_6H_5$ and Y and Z may be, independently of one another, oxygen, sulphur, N—($C_1$-$C_6$)alkyl, N—$C_6H_5$, $CH_2$, $C(CH_3)_2$ or $C(C_6H_5)_2$, wherein two or more adjacent carbon atoms of this —Y—$(CX_2)_p$—Z— grouping, in each case independently of one another, may be part of a benzo ring system fused thereto which, in each case again, can exhibit one or more substituents chosen from the α group or the χ group;

or c) B and B' forming, together with the adjacent carbon atom of the pyran ring, an unsubstituted, monosubstituted or disubstituted 9,10-dihydroanthracene, fluorene, thioxanthene, xanthene, benzo[b]fluorene, 5H-dibenzo[a,d]cycloheptene or dibenzosuberone radical or a saturated hydrocarbon radical which is ($C_3$-$C_{12}$)spiromonocyclic, ($C_7$-$C_{12}$)spirobicyclic or ($C_7$-$C_{12}$)spirotricyclic, wherein the substituents of the unsaturated cyclene may be chosen, independently of one another, from the α group or the χ group.

2. The photochromic benzopyranobenzopyrans according to claim 1, which exhibit the following general formula (II):

(II)

in which B, B', $R_3$, $R_4$, $R_5$, $R_6$, $R_7$ and $R_8$ are as defined above, $R_{16}$ is chosen from the α group and n is 0, 1, 2, 3 or 4.

3. The photochromic benzopyranobenzopyrans according to claim 2, the $R_3$ and $R_4$ radicals being chosen, in each case independently of one another, from the α group.

4. The photochromic benzopyranobenzopyrans according to claim 2, B and B' being chosen, independently of one another, from the group a).

5. The photochromic benzopyranobenzopyrans according to claim 2, which exhibit the following general formulae (III) or (IV):

(III)

(IV)

in which B, B', $R_3$, $R_4$, $R_5$, $R_8$, $R_{10}$ and $R_{16}$ are as defined above and W symbolizes the abovementioned bridging.

6. The photochromic benzopyranobenzopyrans according to claim 2, which exhibit the following general formulae (V), (VI) or (VII):

(V)

(VI)

(VII)

in which B, B', $R_3$, $R_4$, $R_5$, $R_6$, $R_7$, $R_8$, $R_{16}$ and n are as defined above, $R_{17}$ and $R_{18}$ are chosen from the α group and o and q are, independently of one another, 0, 1, 2, 3 or 4.

7. The photochromic benzopyranobenzopyrans according to claim 2, the $R_3$ and $R_4$ radicals being chosen, in each case independently of one another, from the α group, and B and B' being chosen, independently of one another, from the group a).

8. The photochromic benzopyranobenzopyrans according to claim 2, which exhibit the following general formulae (III) or (IV):

(III)

(IV)

in which B, B', $R_3$, $R_4$, $R_5$, $R_8$, $R_{10}$ and $R_{16}$ are as defined above and W symbolizes the abovementioned bridging, and the $R_3$ and $R_4$ radicals being chosen, in each case independently of one another, from the α group.

9. The photochromic benzopyranobenzopyrans according to claim 2, which exhibit the following general formulae (V), (VI) or (VII):

(V)

(VI)

in which B, B', $R_3$, $R_4$, $R_5$, $R_6$, $R_7$, $R_8$, $R_{16}$ and n are as defined above, $R_{17}$ and $R_{18}$ are chosen from the α group and o and q are, independently of one another, 0, 1, 2, 3 or 4, and the $R_3$ and $R_4$ radicals being chosen, in each case independently of one another, from the α group.

10. The photochromic benzopyranobenzopyrans according to claim 2, which exhibit the following general formulae (III) or (IV):

in which B, B', $R_3$, $R_4$, $R_5$, $R_8$, $R_{10}$ and $R_{16}$ are as defined above and W symbolizes the abovementioned bridging, the $R_3$ and $R_4$ radicals being chosen, in each case independently of one another, from the α group, and B and B' being chosen, independently of one another, from the group a).

11. The photochromic benzopyranobenzopyrans according to claim 2, which exhibit the following general formulae (V), (VI) or (VII):

in which B, B', $R_3$, $R_4$, $R_5$, $R_6$, $R_7$, $R_8$, $R_{16}$ and n are as defined above, $R_{17}$ and $R_{18}$ are chosen from the α group and o and q are, independently of one another, 0, 1, 2, 3 or 4, the $R_3$ and $R_4$ radicals being chosen, in each case independently of one another, from the α group, and B and B' being chosen, independently of one another, from the group a).

12. The photochromic benzopyranobenzopyrans according to claim 1, the $R_3$ and $R_4$ radicals being chosen, in each case independently of one another, from the α group.

13. The photochromic benzopyranobenzopyrans according to claim 12, B and B' being chosen, independently of one another, from the group a).

14. The photochromic benzopyranobenzopyrans according to claim 12, which exhibit the following general formulae (III) or (IV):

in which B, B', $R_3$, $R_4$, $R_5$, $R_8$, $R_{10}$ and $R_{16}$ are as defined above and W symbolizes the abovementioned bridging.

15. The photochromic benzopyranobenzopyrans according to claim 12, which exhibit the following general formulae (V), (VI) or (VII):

in which B, B', $R_3$, $R_4$, $R_5$, $R_6$, $R_7$, $R_8$, $R_{16}$ and n are as defined above, $R_{17}$ and $R_{18}$ are chosen from the α group and o and q are, independently of one another, 0, 1, 2, 3 or 4.

16. The photochromic benzopyranobenzopyrans according to claim 1, B and B' being chosen, independently of one another, from the group a).

17. The photochromic benzopyranobenzopyrans according to claim 16, which exhibit the following general formulae (III) or (IV):

(IV)

in which B, B', $R_3$, $R_4$, $R_5$, $R_8$, $R_{10}$ and $R_{16}$ are as defined above and W symbolizes the abovementioned bridging.

18. The photochromic benzopyranobenzopyrans according to claim 16, which exhibit the following general formulae (V), (VI) or (VII):

(V)

(VI)

(VII)

in which B, B', $R_3$, $R_4$, $R_5$, $R_6$, $R_7$, $R_8$, $R_{16}$ and n are as defined above, $R_{17}$ and $R_{18}$ are chosen from the α group and o and q are, independently of one another, 0, 1, 2, 3 or 4.

19. The photochromic benzopyranobenzopyrans according to claim 16, which exhibit the following general formulae (III) or (IV):

(III)

(IV)

in which B, B', $R_3$, $R_4$, $R_5$, $R_8$, $R_{10}$ and $R_{16}$ are as defined above and W symbolizes the abovementioned bridging, and the $R_3$ and $R_4$ radicals being chosen, in each case independently of one another, from the α group.

20. The photochromic benzopyranobenzopyrans according to claim 16, which exhibit the following general formulae (V), (VI) or (VII):

(V)

(VI)

(VII)

in which B, B', $R_3$, $R_4$, $R_5$, $R_6$, $R_7$, $R_8$, $R_{16}$ and n are as defined above, $R_{17}$ and $R_{18}$ are chosen from the α group and o and q are, independently of one another, 0, 1, 2, 3 or 4, and the $R_3$ and $R_4$ radicals being chosen, in each case independently of one another, from the α group.

21. The photochromic benzopyranobenzopyrans according to claim 1, which exhibit the following general formulae (III) or (IV):

(III)

(IV)

in which B, B', $R_3$, $R_4$, $R_5$, $R_8$, $R_{10}$ and $R_{16}$ are as defined above and W symbolizes the abovementioned bridging formed by $R_9$ or $R_{10}$ with $R_6$ or $R_7$, respectively.

22. The photochromic benzopyranobenzopyrans according to claim 1, which exhibit the following general formulae (V), (VI) or (VII):

(V)

(VI)

(VII)

in which B, B', $R_3$, $R_4$, $R_5$, $R_6$, $R_7$, $R_8$, $R_{16}$ and n are as defined above, $R_{17}$ and $R_{18}$ are chosen from the α group and o and q are, independently of one another, 0, 1, 2, 3 or 4.

23. A process comprising adding the photochromic benzopyranobenzopyrans according to claim 1, in an admixture with and/or application on plastic or glass materials.

24. The process according to claim 23, the plastic material being an ophthalmic lens.

* * * * *